United States Patent
Song et al.

(10) Patent No.: US 11,497,612 B1
(45) Date of Patent: Nov. 15, 2022

(54) FEMORAL NECK PRESERVING STEM HIP IMPLANT

(71) Applicant: Omnes Medical Inc., Houston, TX (US)

(72) Inventors: Benjamin Sooil Song, Los Angeles, CA (US); Ilwhan Park, Katy, TX (US); Khatereh Hajizadeh, San Jose, CA (US)

(73) Assignee: Omnes Medical, Inc., Houston, TX (US)

( * ) Notice: Subject to any disclaimer, the term of this patent is extended or adjusted under 35 U.S.C. 154(b) by 0 days.

(21) Appl. No.: 17/159,050

(22) Filed: Jan. 26, 2021

Related U.S. Application Data

(60) Provisional application No. 62/966,457, filed on Jan. 27, 2020.

(51) Int. Cl.
*A61F 2/36* (2006.01)
*A61F 2/34* (2006.01)
*A61F 2/30* (2006.01)

(52) U.S. Cl.
CPC ........ *A61F 2/3609* (2013.01); *A61F 2/30749* (2013.01); *A61F 2/34* (2013.01); *A61F 2/367* (2013.01); *A61F 2002/30354* (2013.01); *A61F 2002/30494* (2013.01); *A61F 2002/365* (2013.01); *A61F 2002/3611* (2013.01);
(Continued)

(58) Field of Classification Search
CPC ........ A61F 2/36; A61F 2/3601; A61F 2/3609; A61F 2/367; A61B 17/72; A61B 17/725; A61B 17/7241; A61B 17/74
See application file for complete search history.

(56) References Cited

U.S. PATENT DOCUMENTS 7,569,075 B2   8/2009  Johnson et al.
8,579,985 B2 * 11/2013  Podolsky ........... A61B 17/7283
                                                     623/22.42
(Continued)

OTHER PUBLICATIONS

A.J. Wassef et al., "Use of an offset head center acetabular shell in difficult primary total hip arthroplasties", Annals of Translational Medicine, 2019, 7(4):75, 7 pages.
(Continued)

*Primary Examiner* — Brian A Dukert
(74) *Attorney, Agent, or Firm* — Mark Protsik; Thomas Schneck

(57) ABSTRACT

The femoral neck preserving hip implant includes a polymer femoral head molded onto a femoral head base, which is attached to a femoral neck rod to be inserted into the femoral neck of a patient. A metal acetabular cup is inserted into an acetabulum anatomy of a pelvis. The femoral head interfaces with the acetabular cup as a smooth plastic-to-metal spherical-surface joint. A main body shaft to be inserted into a femoral shaft has a diagonal hole therethrough located at a center line of the femur's neck to receive the femoral neck rod at a specified angle. A secured lock mechanism in the main body shaft above the diagonal hole is screwed down to compressively engage the femoral neck rod. Both the diagonal hole and the end of the femoral neck rod may have a slight taper. The femoral neck rod also has a radially outward extending flange that forms a contact feature that sits upon the resection plane of the femoral neck to stabilize against axial force loading.

11 Claims, 11 Drawing Sheets

(52) U.S. Cl.
CPC .......... *A61F 2002/3625* (2013.01); *A61F 2002/3652* (2013.01); *A61F 2310/00017* (2013.01); *A61F 2310/00023* (2013.01); *A61F 2310/00059* (2013.01)

(56) References Cited

U.S. PATENT DOCUMENTS

| | | | |
|---|---|---|---|
| 3,840,675 | A1 | 9/2014 | Song |
| 9,433,448 | B2 * | 9/2016 | Ehmke .............. A61B 17/744 |
| 2014/0180289 | A1 * | 6/2014 | Lee ..................... A61F 2/36 606/64 |
| 2020/0129298 | A1 * | 4/2020 | Kavolus, II ......... A61F 2/3609 |

OTHER PUBLICATIONS

M. Scaglione et al., "Hip replacement in femoral head osteonecrosis: current concepts", Clinical Cases in Mineral and Bone Metabolism 2015, 12(Suppl. 1), pp. 51-54, 4 pages.
K. Issa et al., "Hip pathologies that bedevil—Osteonecrosis of the femoral head: The total hip replacement solution", CCJR Supplemental to The Bone & Joint Journal, vol. 95-B, No. 11, Nov. 2013, pp. 46-50, 5 pages.
V.C. Bose et al., "Resurfacing arthroplasty of the hip for avascular necrosis of the femoral head", The Journal of Bone and Joint Surgery, vol. 92-B, 922-8, Mar. 16, 2010, 7 pages.

\* cited by examiner

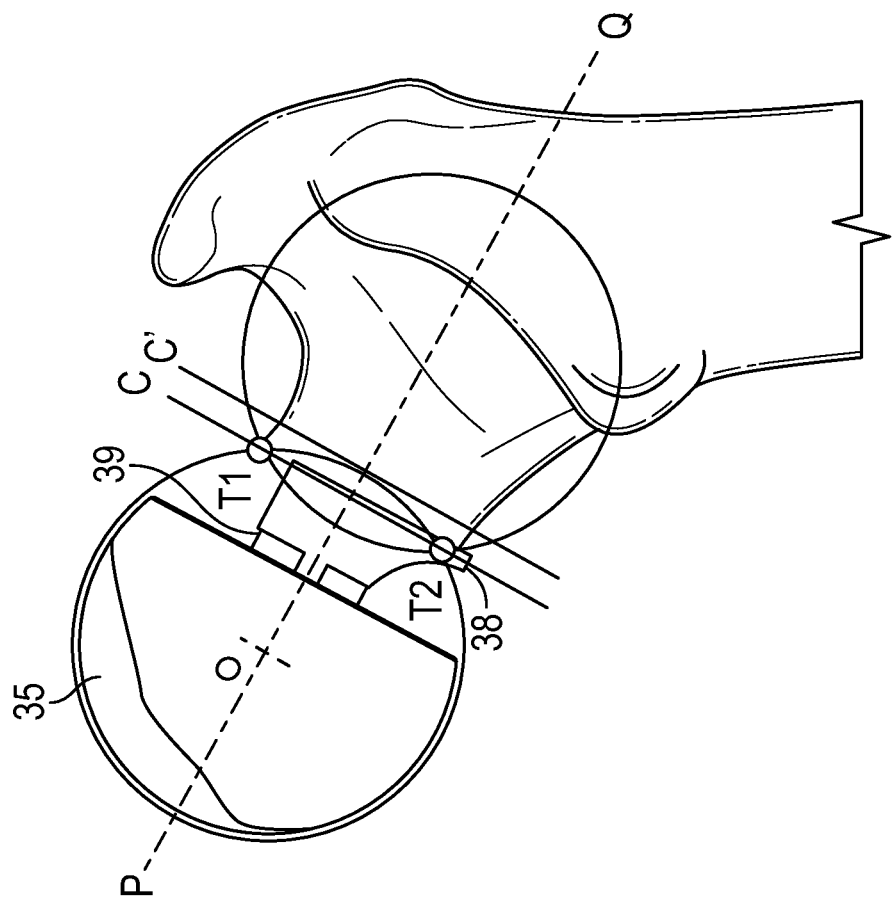
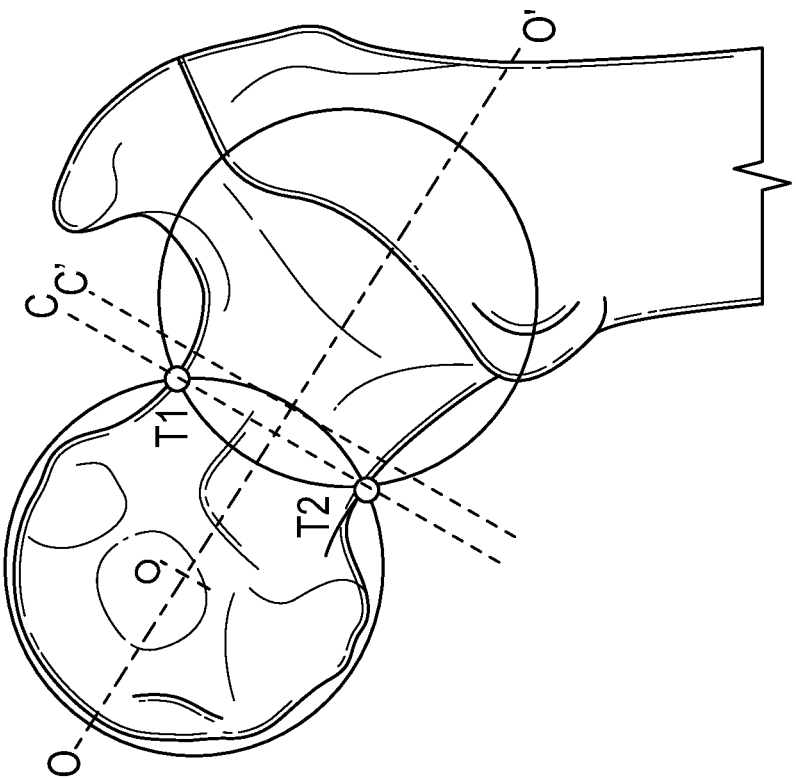

US 11,497,612 B1

FEMORAL NECK PRESERVING STEM HIP IMPLANT

CROSS-REFERENCE TO RELATED APPLICATION

This application claims priority under 35 U.S.C. 119(e) from U.S. provisional application No. 62/966,457 filed Jan. 27, 2020.

TECHNICAL FIELD

The present invention relates to hip implants for total hip replacement of the acetabular-femoral joint and adapted for improved durability in those patients having or likely to develop osteonecrosis, not only in the femoral head but also in the femoral neck.

BACKGROUND ART

Osteonecrosis (also known as avascular necrosis) is a chronic disease caused by reduced blood flow to bone tissue near the joints. In people with healthy bones, new bone is always replacing old bone. In osteonecrosis, the lack of blood causes the bone to break down faster than the body can make enough new bone. The bone starts to die and may break down. FIGS. 1A and 1B show a normal femoral head 11 and an osteonecrosis femoral head 12, respectively. In FIG. 1B, the severe osteonecrosis is seen to have caused a breakdown of the femoral head 12.

FIGS. 2A and 2B show a prior art thrust plate design with primary fixation through the press-fit of the thrust plate 15 in the femoral neck and compression achieved through the bolt 17 that passes from the lateral cortex.

A hip resurfacing implant 21 requires arthritis femoral head 23 without osteonecrosis, or at least early stage of osteonecrosis, as shown in FIGS. 3A-3C.

FIGS. 4A and 4B show the severe case of femoral neck osteonecrosis 25 that does not provide enough volume to makes hip resurfacing implants difficult to use.

SUMMARY DISCLOSURE

The implant includes an acetabular cup configured to be inserted into an acetabulum anatomy of a pelvis. A femoral head is molded onto a femoral head base, which in turn is attached to a femoral neck rod that is configured to be inserted along a center line into the neck of a patient's femur. The femoral head is composed of a bio-compatible polymer, while the acetabular cup, femoral head base, and femoral neck rod are composed of a bio-compatible metal. Thus, the femoral head is configured to interface with the acetabular cup as a smooth plastic-to-metal spherical-surface joint.

A main body shaft of the implant is configured to be inserted into a femoral shaft region of a patient's femur (and secured by horizontal bone screws through cortical bone of the femur). This main body shaft is likewise composed of a bio-compatible metal. It has a linear central axis that extends the entire length of the shaft and has a diagonal hole therethrough that is located at a center line of the femur's neck to receive the femoral neck rod at a specified angle. Both the diagonal hole and the end of the femoral neck rod that inserts into the diagonal hole may have a slight taper. A secured lock mechanism inserted into the main body shaft above the diagonal hole is screwed down to compressively engage the femoral neck rod and stabilize. A feature of the femoral neck rod is the presence near the femoral head base of a radially outward extending flange that forms a contact feature that sits upon the resection plane of the femoral neck to further stabilize against axial force loading of the femoral neck rod.

BRIEF DESCRIPTION OF THE DRAWINGS

FIGS. 10A and 10B are side views of an upper femur respectively before and after implantation, with overlaid geometries that illustrate the surgical planning and placement for a femoral head and neck implant in accord with the present invention.

DETAILED DESCRIPTION

The implant parts described herein are made from a combination of bio-compatible metals and bio-compatible polymers. Bio-compatible metals can include any of cobalt, chromium, titanium, alloys thereof, and medical-grade stainless steel 316 (UNS S31603/SAE 316L/ASTM A240). More recently, nitrogen-strengthened austenitic stainless steels that are low-nickel or nickel-free (e.g., UNS S29108/ASTM F2290-20, and UNS S29225/ASTM F2581-12) have become available for use in surgical implants to avoid adverse effects of nickel ions in the human body while maintaining high strength and wear resistance. Bio-compatible polymers can include any of polyethylene, polyether ether ketone (PEEK), and ultra-high-molecular-weight polyethylene (UHMWPE).

Figure 1A:
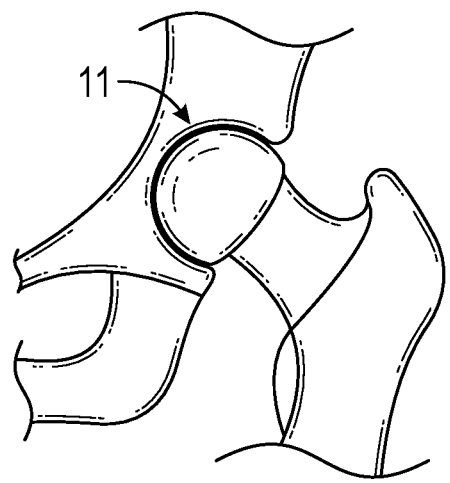
FIGS. 1A and 1B are coronal side view anatomical sketches that illustrate a normal femoral head and an osteonecrosis femoral head, respectively.
Figure 1B:
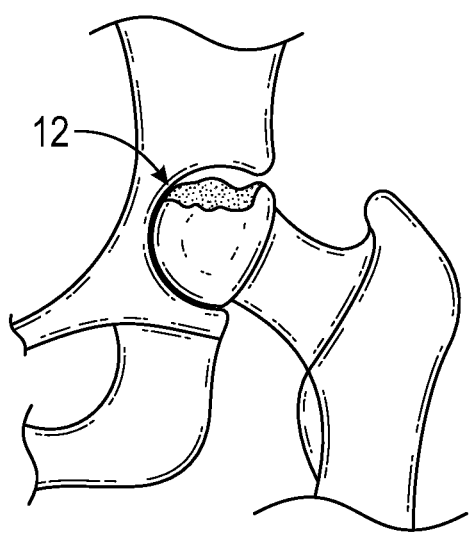
Figure 2B:
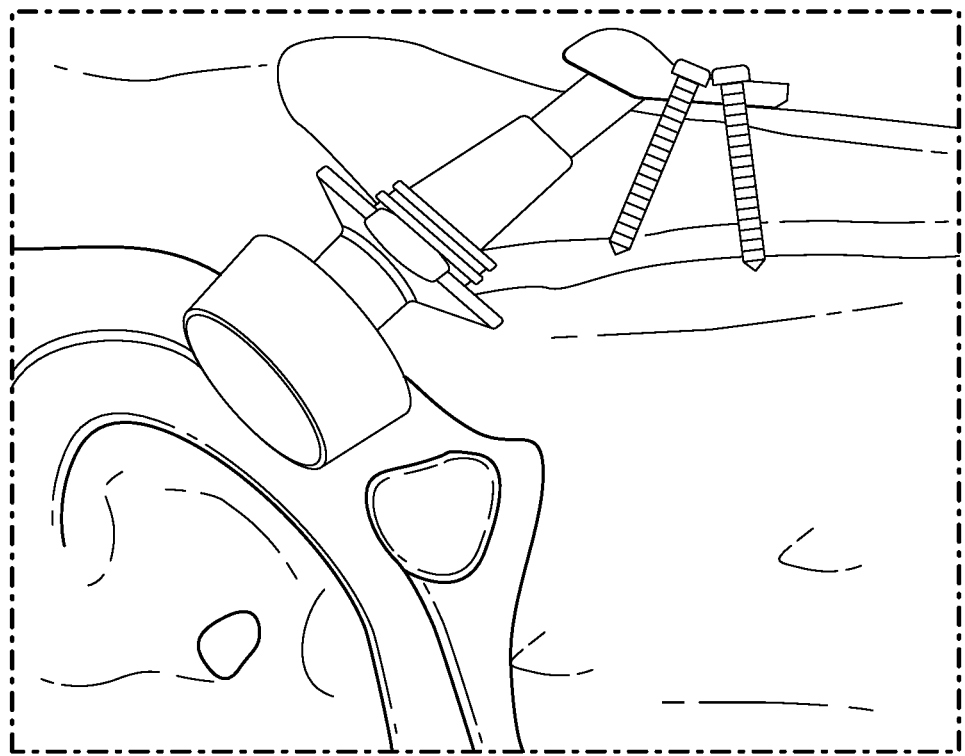
FIGS. 2A and 2B are, respectively, a perspective of a prior art thrust-plate femoral neck implant and a corresponding coronal MRI image of the implant installed in a patient's femur.
Figure 2A:
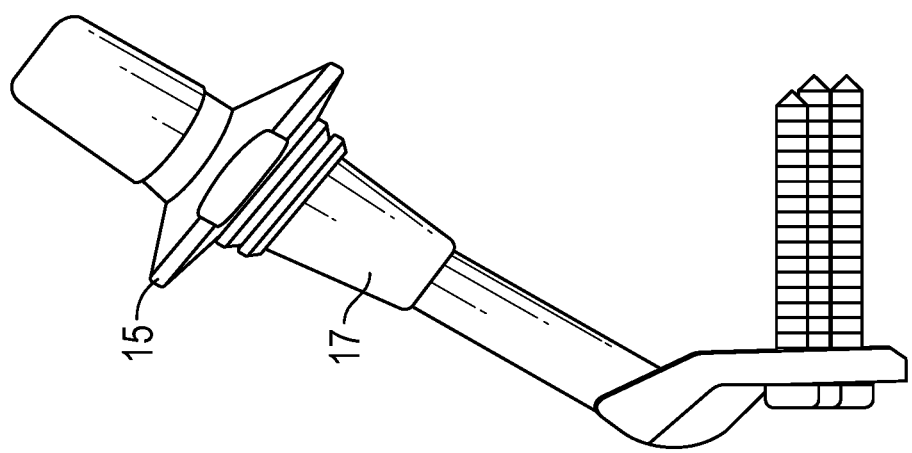
Figure 3A:
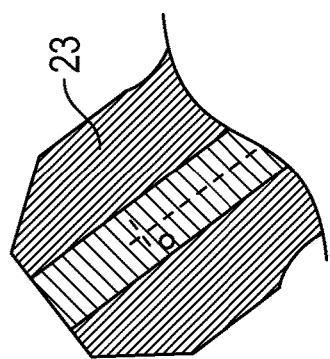
FIGS. 3A-3C are a side sectional view of a hip resurfacing implant, a coronal MRI image of a femoral head minimal osteonecrosis showing an overlay of the implant's placement, and a corresponding MRI image with the implant's placement overlaid relative to a femoral head with early-stage osteonecrosis, respectively.
Figure 3B:
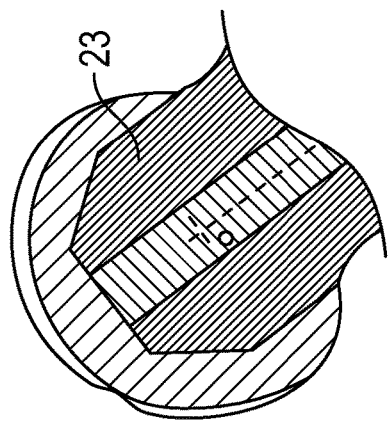
Figure 3C:
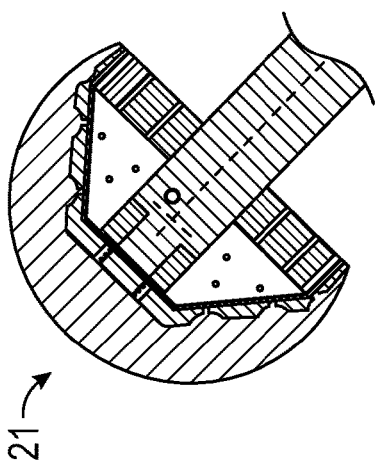
Figure 4A:
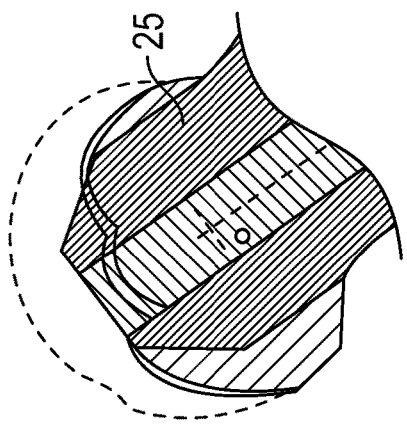
FIGS. 4A-4B are coronal MRI images of two femoral heads with overlaid hip resurfacing implant placements, one for the case with minimal osteonecrosis and the other with severe osteonecrosis, illustrating that there is insufficient volume in severe cases of femoral neck osteonecrosis, which makes it difficult to use a hip resurfacing implant.
Figure 4B:
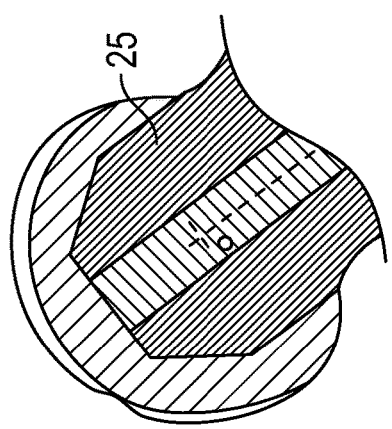
Figure 5A:
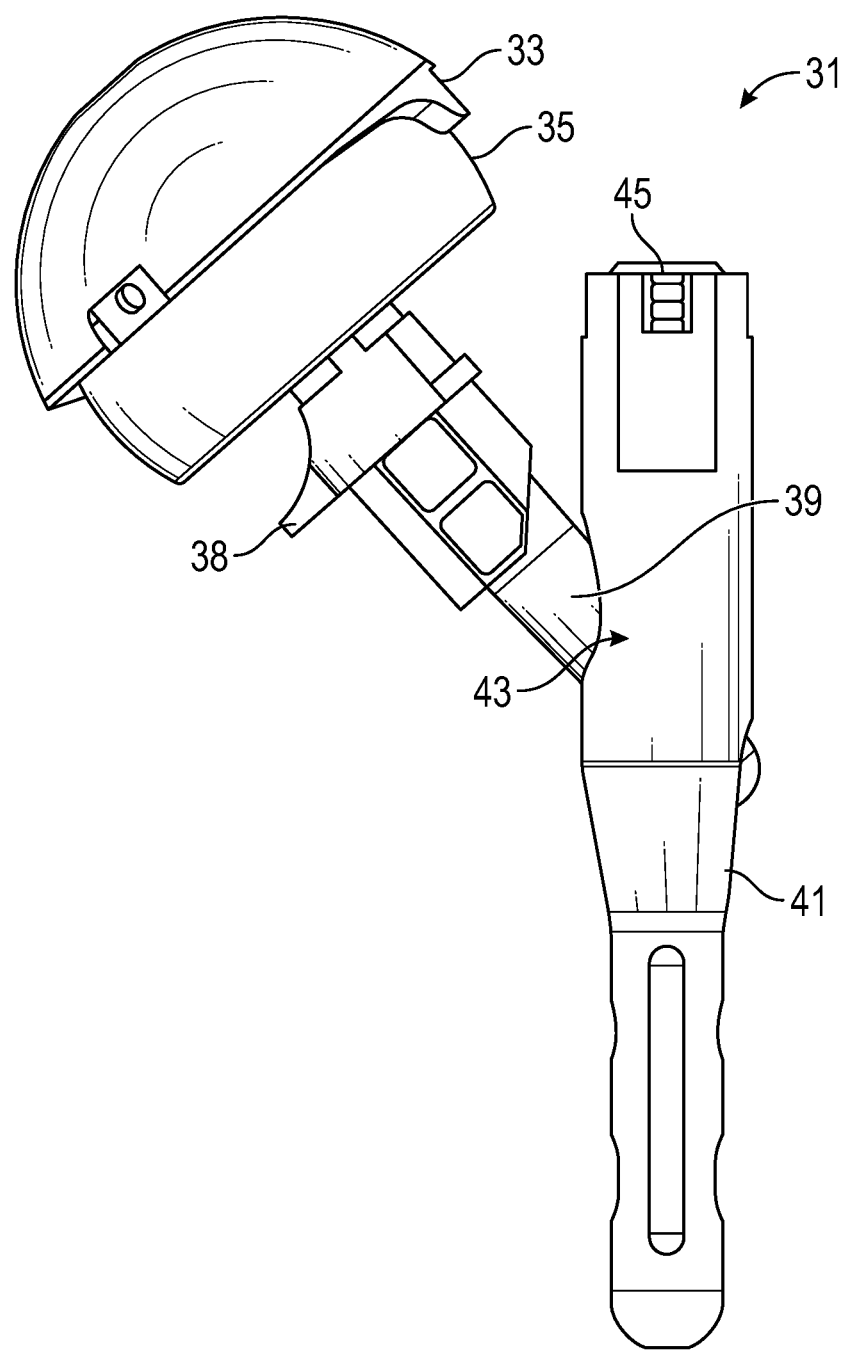
FIGS. 5A and 5B are side plan and sectional views that show a total hip replacement implant according to the present invention for patients with severe femoral head osteonecrosis.
Figure 5B:
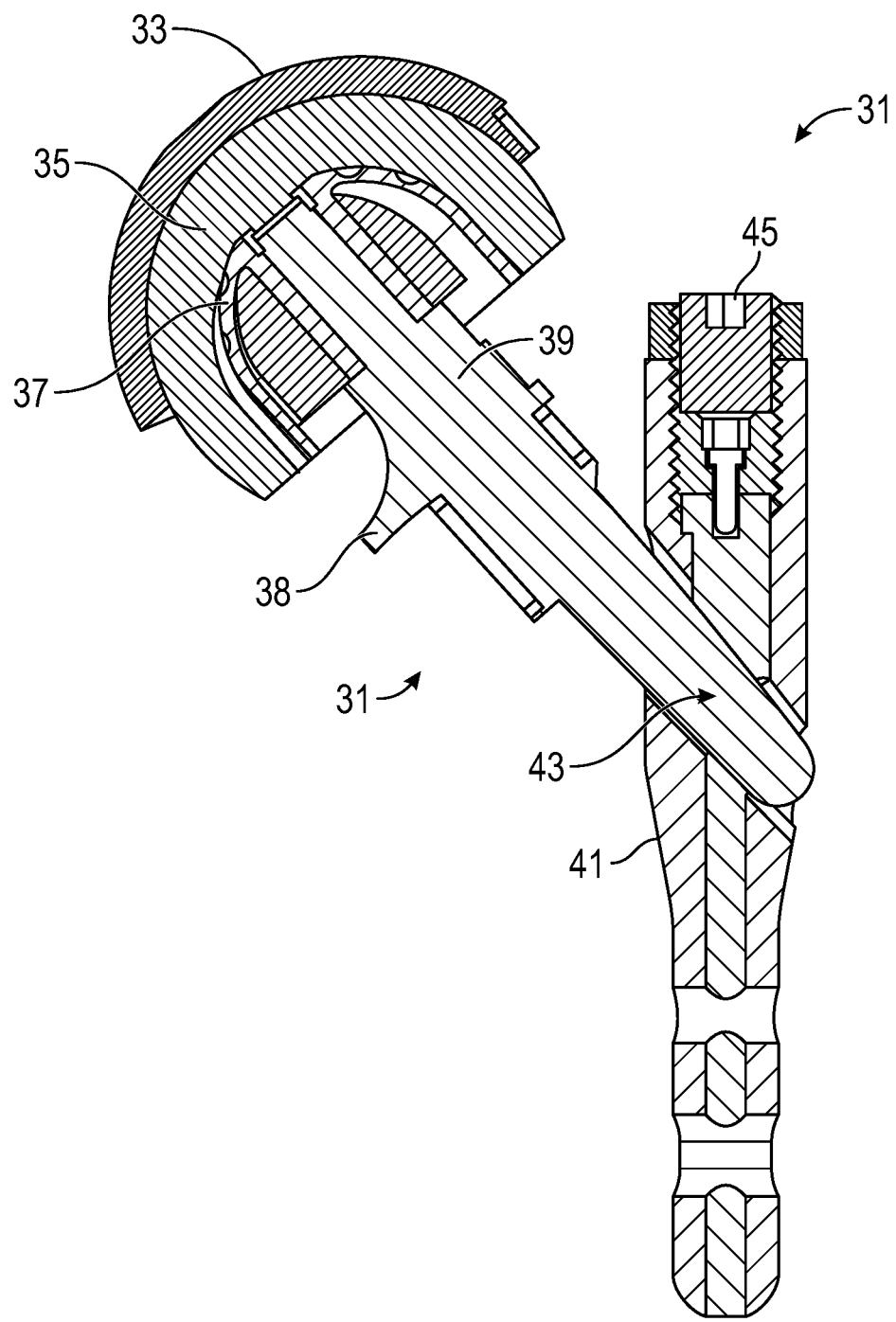

FIGS. 5A and 5B are side plan and sectional views that show a total hip replacement implant 31 according to the present invention for patients with severe femoral head osteonecrosis. The implant includes an acetabular cup 33 configured to be inserted into an acetabulum anatomy of a pelvis. A femoral head 35 is molded onto a femoral head base 37, which in turn is attached to a femoral neck rod 39 that is configured to be inserted along a center line into the neck of a patient's femur. The femoral head 35 is configured to interface with the acetabular cup 33 as a smooth spherical-surface joint. The femoral head 35 is composed of a bio-compatible polymer. The acetabular cup 33, as well as the femoral head base 37 and femoral neck rod 39, are composed of a bio-compatible metal. Thus, the spherical-surface joint formed by the femoral head and acetabular cup create a smooth plastic-to-metal joint.

Also, seen in FIGS. 5A-5B are a main body shaft 41 of the implant 31 that is configured to be inserted into a femoral shaft region of a patient's femur (and secured by horizontal bone screws through cortical bone of the femur). This main body shaft 41 is likewise composed of a bio-compatible metal. It has a linear central axis that extends the entire length of the shaft and has a diagonal hole 43 therethrough that is located at a center line of the femur's neck to receive the femoral neck rod 39 at a specified angle in a range from about 132° to 140° relative to the linear central axis. Both the diagonal hole 43 and the end of the femoral neck rod 39 that inserts into the diagonal hole 43 may have a slight taper angle in a range from 2° to 4°. A secured lock mechanism 45 inserted into the main body shaft 41 above the diagonal hole 43 can be screwed down to compressively engage the femoral neck rod 39 and stabilize axial force loading of the femoral neck rod 39.

A feature of the femoral neck rod 39 is the presence near the femoral head base 37 of a radially outward extending flange 38 that forms a contact feature that sits upon the resection plane of the femoral neck.

Figure 6A:
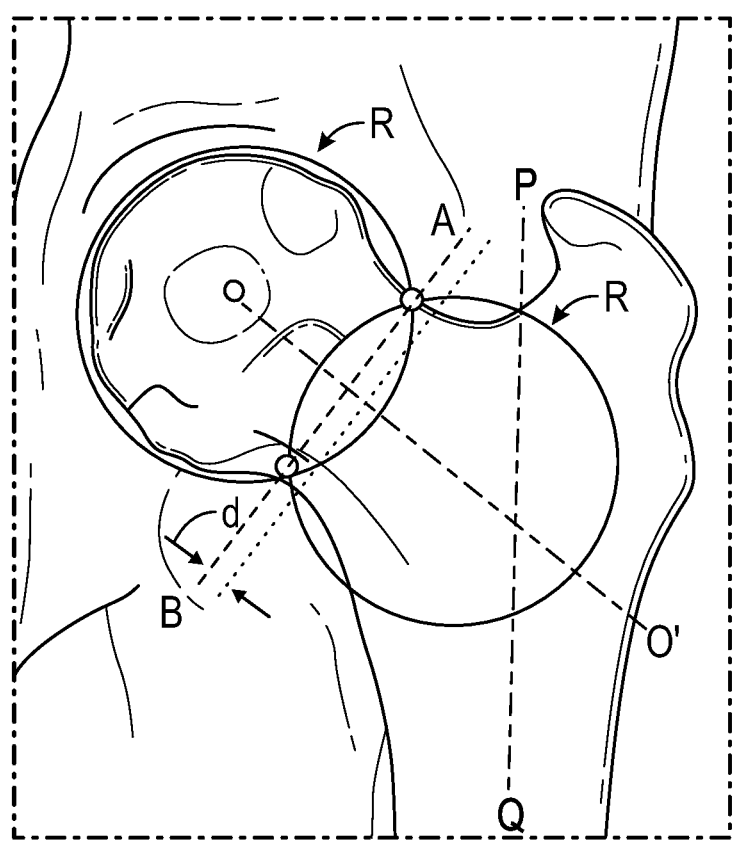
FIGS. 6A and 6B are a coronal MRI scan of a patient's hip and a sectional view of the implant of FIGS. 5A and 5B, both overlaid with geometries that illustrate the implant design specifications for both acetabulum cup and femoral component of the implant.
Figure 6B:
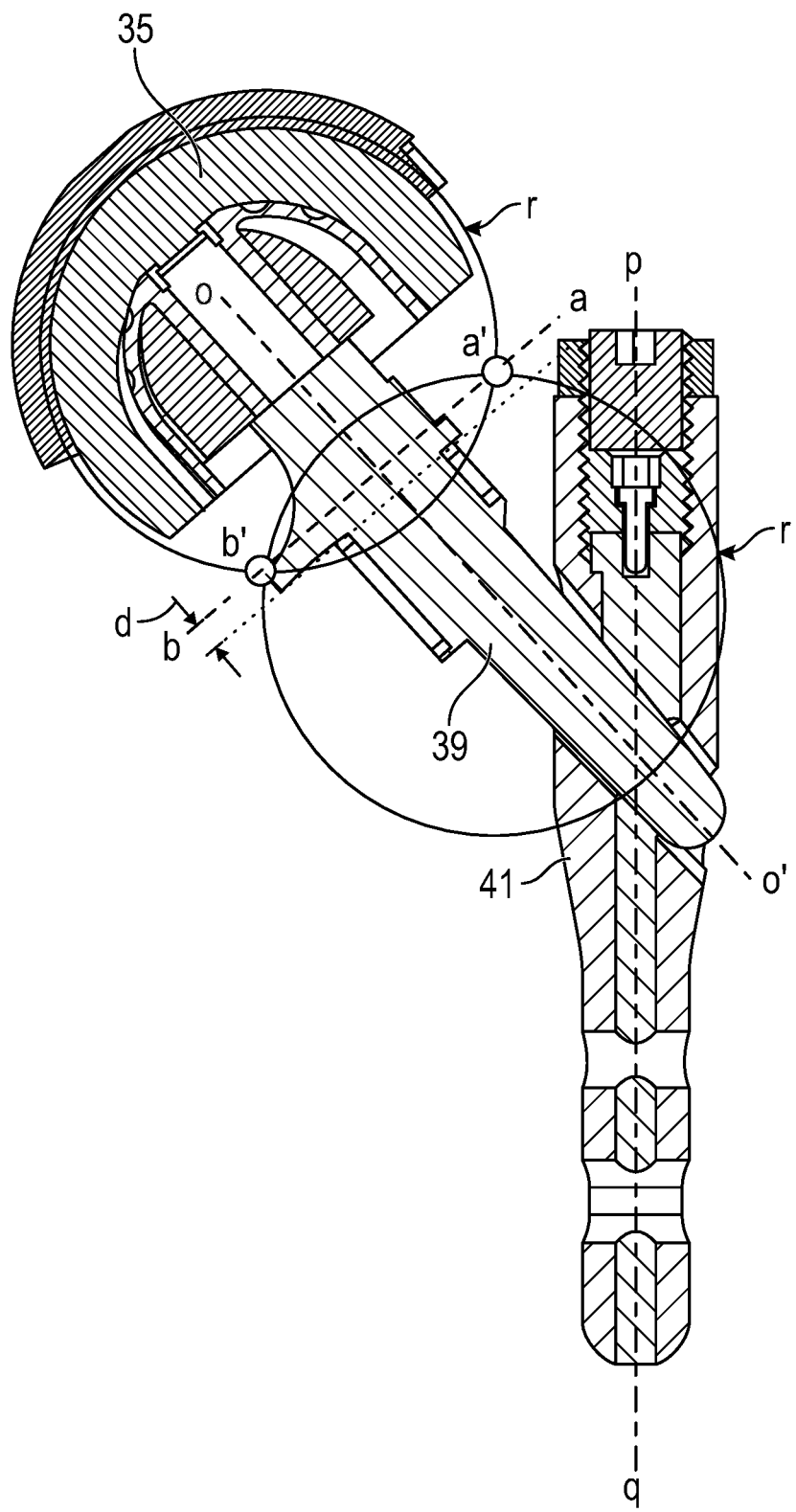

FIGS. 6A and 6B are a coronal MRI scan of a patient's hip and a sectional view of the implant of FIGS. 5A and 5B, both overlaid with geometries that illustrate the implant design specifications for both acetabulum cup and femoral component of the implant. It shows the intended anatomical relation between the acetabulum size and femoral neck 39 to trochanter. The line O-O' is the center line of the femoral neck, with point O at the center of the femoral head 35. The line P-Q is the central axis of the femoral shaft 41. Two overlapping circles of radius R are seen, matching the radius of curvature of the acetabulum and femoral head surface. One circle is centered at point O, while the second circle is centered upon the line O-O' at a position such that the trochanter, line P-Q, and the circle coincide. The two circles overlap at points A' and B', which define a line A-B. The cut plane is determined a distance d in a range from 2 to 4 mm to the lateral direction with respect to impinging line A-B. The selection of implant is determined by $R = r + \varepsilon$, where $\varepsilon \ll 1$.

Figure 7:
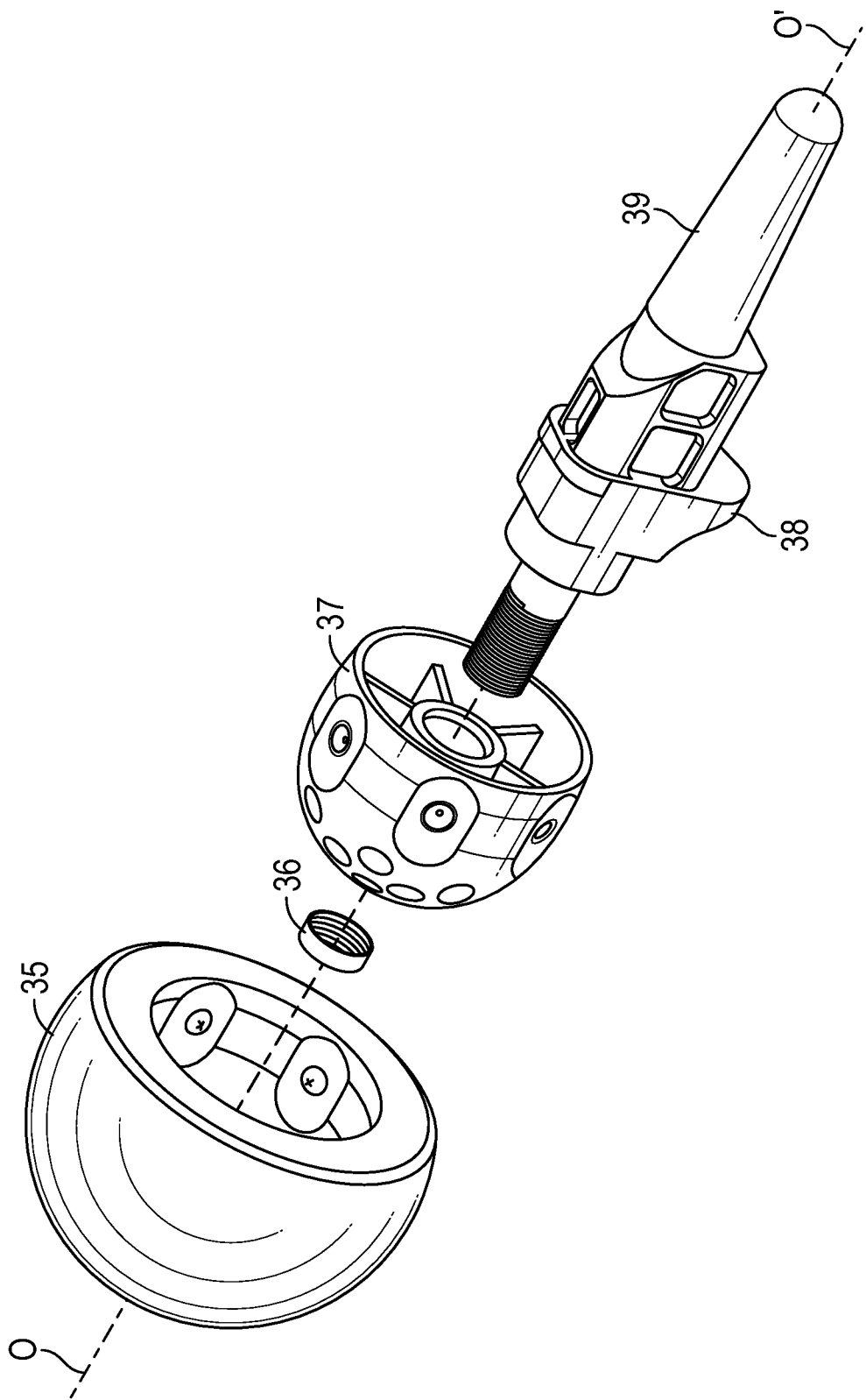
FIG. 7 is an exploded perspective view of the implant of FIGS. 5A and 5B that shows disassembled femoral head and neck components.

FIG. 7 is an exploded perspective view showing disassembled femoral head and neck components 35-39 of the implant of FIGS. 5A and 5B. The femoral head and neck components comprise a bio-compatible polymer (e.g., UHMWPE) femoral head 35 molded onto a bio-compatible metal base 37. An implant femoral neck 39 screws into the metal base 37 and is secured by a securing nut 36 prior to the molding process. The extending flange 38 of the femoral neck 39 is also seen.

Figure 8A:
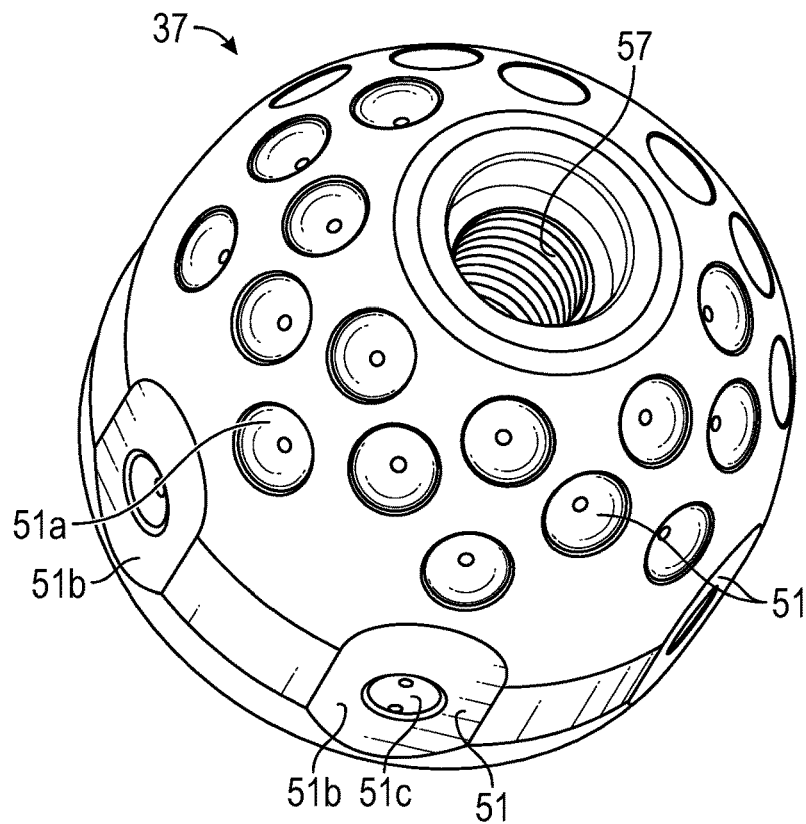
FIGS. 8A and 8B are exterior and interior perspective views that show details of the metal base of the femoral head component of FIG. 7.
Figure 8B:
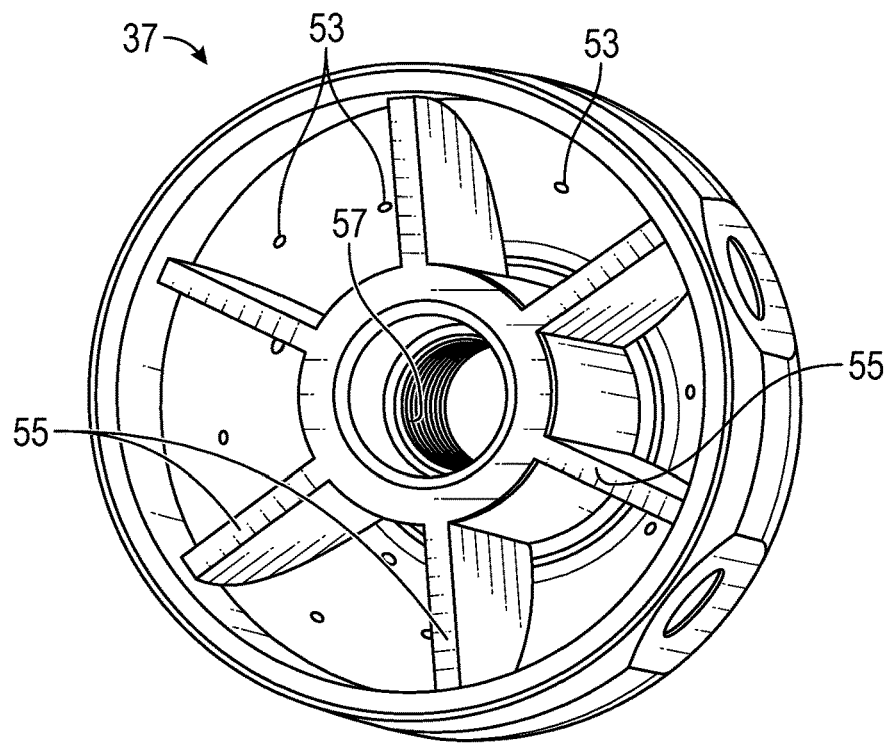

FIGS. 8A and 8B are exterior and interior perspective views that show details of the metal base 37 of the femoral head component of FIG. 7. The metal base includes polyethylene structural stabilizer features 51 to secure the translation and rotation of polyethylene femoral head 35 molded onto the femoral head metal base 37. Specifically, a set of dimples 51a are provided in the surface of the femoral head base 37. A set of shallow mounds 51b, each with its own central dimples 51c, are provided around the periphery of the femoral head base 37 to stabilize the femoral head against rotational forces. Together, these stabilizer features 51 create a stable interface between the polymer femoral head and the metallic femoral head base. To enhance compressed molding, molding holes 53 are also included in this design. Also, as seen in FIG. 8B, the inner features include structural reinforcement ribs 55 with threaded neck-receiving feature 57 at the center.

Figure 9A:
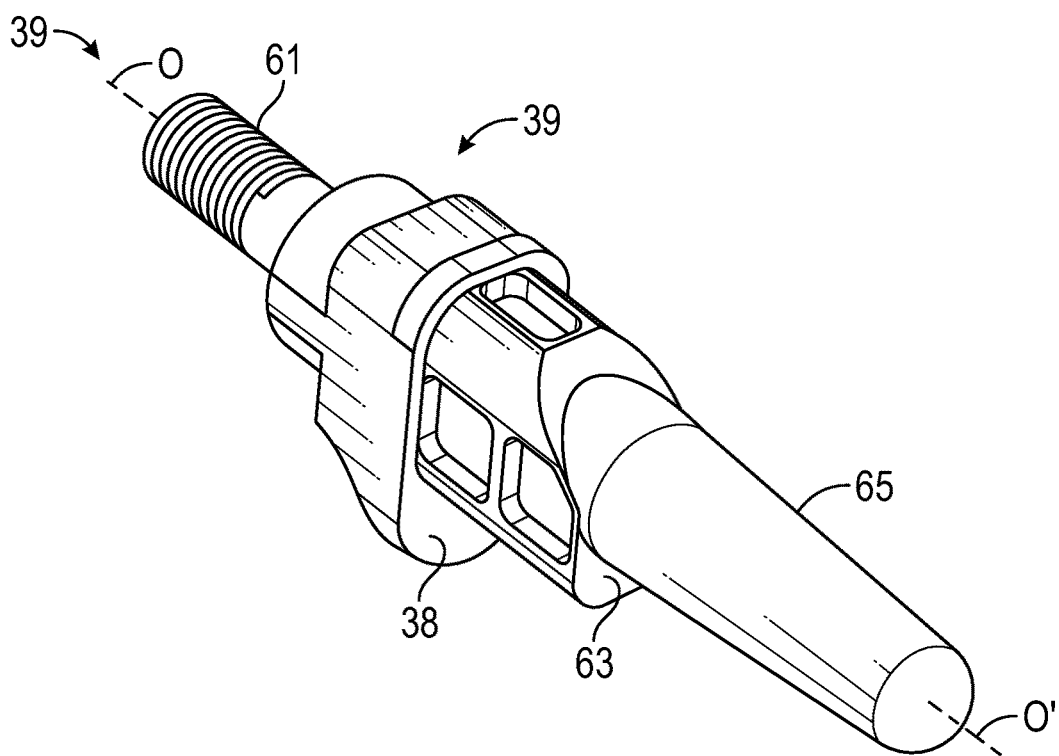
FIGS. 9A and 9B are two perspective views that show the implant femoral neck component of FIG. 7.
Figure 9B:
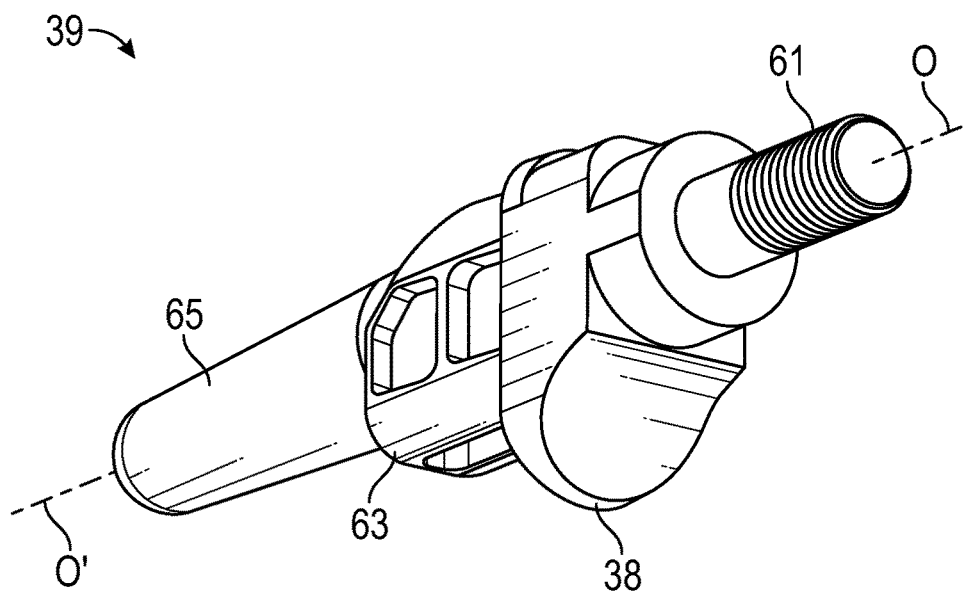

FIGS. 9A and 9B are two perspective views that show the implant femoral neck component 39 of FIG. 7. One feature is a femoral neck thread 61 to screw into the implant femoral head metal base and securing nut. Additionally, as previously mentioned, a femoral neck contact feature 38 is introduced to sit on the resection plane of the femoral neck. Bone cement can be applied on this feature. Also, a double rectangular-shaped box 63 is introduced for structural stability against rotation with respect to the center axis OO' of the femoral neck rod. The double rectangular box 63 includes the bone cement placement feature 64. The tapered rod 65 is introduced for additional axial stability along the center axis O-O'.

FIGS. 10A and 10B are side views of an upper femur respectively before and after implantation, with overlaid geometries that illustrate the surgical planning and placement for a femoral head 35 and neck 39 implant in accord with the present invention. The cut plane C is, as previously mentioned above with reference to FIGS. 6A and 6B, about 2 to 4 mm in a lateral direction from the line A-B in that figure. The femoral neck rod's 39 contact feature 38 sits on cut plane C' slightly displaced from a line AB between A' and B'.

The invention claimed is:

1. A hip implant, comprising:
   an acetabular cup configured to be inserted into an acetabulum anatomy of a pelvis, the acetabular cup composed of a bio-compatible metal;
   a femoral head and neck portion with a femoral head composed of a bio-compatible polymer molded onto a bio-compatible metal femoral head base that is attached to a bio-compatible metal femoral neck rod, the femoral head configured to interface with the acetabular cup as a smooth plastic-to-metal spherical-surface joint, the femoral neck rod configured to be inserted along a center line into a neck of the femur, the femoral neck rod having a radially outward extending flange that forms a contact feature configured to sit upon a resection plane of the neck of the femur, the femoral head base having a set of structural stabilizer features on its surface providing a secure interface with the respective femoral head and femoral neck portions of the implant, the stabilizer features of the femoral head base comprising a set of dimples over its surface onto which the femoral head is molded, a set of shallow mounds with central dimples therein provided around a periphery of the femoral head, a set of molding holes through the femoral head base, and a set of reinforcement ribs for a threaded neck rod receiving feature on an otherwise hollow inner portion of the femoral head base; and
   a main body shaft configured to be inserted into a femoral shaft region of the femur and secured by bone screws through cortical bone of the femur, the main body shaft composed of a bio-compatible metal and having a linear central axis that extends an entire length of the main body shaft, the main body shaft also having a diagonal hole therethrough located at the center line of the neck of the femur so as to receive the femoral neck rod at a specified angle that aligns with that center line.

2. The hip implant as in claim 1, wherein the bio-compatible metal comprises any of cobalt, chromium, titanium, alloys thereof, medical-grade stainless steel 316, and nitrogen-strengthened low-nickel and nickel-free stainless steels.

3. The hip implant as in claim 1, wherein the bio-compatible polymer comprises any of polyethylene, polyether ether ketone (PEEK), and ultra-high-molecular-weight polyethylene (UHMWPE).

4. The hip implant as in claim 1, wherein the diagonal hole through the main body shaft is at a specified femoral angle in a range from 132 to 140 degrees.

5. The hip implant as in claim 1, wherein an end of the femoral neck rod has a tapered end with a taper angle in a range from two to four degrees.

6. The hip implant as in claim 1, further comprising a secured lock mechanism insertable into the main body shaft above the diagonal hole that, when screwed down to engage the femoral neck rod, stabilizes axial force loading of the femoral neck rod.

7. A hip implant, comprising:
  an acetabular cup configured to be inserted into an acetabulum anatomy of a pelvis, the acetabular cup composed of a bio-compatible metal;
  a femoral head and neck portion with a femoral head composed of a bio-compatible polymer molded onto a bio-compatible metal femoral head base that is attached to a bio-compatible metal femoral neck rod, the femoral head base having a set of structural stabilizer features on its surface providing a secure interface with the respective femoral head and femoral neck portions of the implant, the stabilizer features of the femoral head base comprising a set of dimples over its surface onto which the femoral head is molded, a set of shallow mounds with central dimples therein provided around a periphery of the femoral head, a set of molding holes through the femoral head base, and a set of reinforcement ribs for a threaded neck rod receiving feature on an otherwise hollow inner portion of the femoral head base, the femoral head configured to interface with the acetabular cup as a smooth plastic-to-metal spherical-surface joint, the femoral neck rod configured to be inserted along a center line into a neck of the femur, the femoral neck rod having a radially outward extending flange that forms a contact feature configured to sit upon a resection plane of the neck of the femur, the femoral neck rod also having a tapered end with a specified taper angle; and
  a main body shaft configured to be inserted into a femoral shaft region of the femur and secured by bone screws through cortical bone of the femur, the main body shaft composed of a bio-compatible metal and having a linear central axis that extends an entire length of the main body shaft, the main body shaft also having a diagonal hole at a specified angle therethrough located at the center line of the neck of the femur to receive the tapered end of the femoral neck rod at the specified angle that aligns with that center line, the main body shaft further having a secured lock mechanism insertable therein above the diagonal hole that, when screwed down to engage the tapered femoral neck rod, stabilizes axial force loading of the femoral neck rod.

8. The hip implant as in claim 7, wherein the bio-compatible metal comprises any of cobalt, chromium, titanium, alloys thereof, medical-grade stainless steel 316, and nitrogen-strengthened low-nickel and nickel-free stainless steels.

9. The hip implant as in claim 7, wherein the bio-compatible polymer comprises any of polyethylene, polyether ether ketone (PEEK), and ultra-high-molecular-weight polyethylene (UHMWPE).

10. The hip implant as in claim 7, wherein the diagonal hole through the main body shaft is at a specified femoral angle in a range from 132 to 140 degrees.

11. The hip implant as in claim 7, wherein the tapered end of the femoral neck rod has a taper angle in a range from two to four degrees.

\* \* \* \* \*